United States Patent [19]

Balasubramanyan et al.

[11] 4,243,405
[45] * Jan. 6, 1981

[54] FUNGICIDAL COMPOUNDS

[75] Inventors: Sugavanam Balasubramanyan, Wokingham; Margaret C. Shephard, Maidenhead, both of England

[73] Assignee: Imperial Chemical Industries Limited, London, England

[*] Notice: The portion of the term of this patent subsequent to Jul. 14, 1995, has been disclaimed.

[21] Appl. No.: 826,263

[22] Filed: Aug. 19, 1977

[30] Foreign Application Priority Data

| | | | |
|---|---|---|---|
| Aug. 19, 1976 | [GB] | United Kingdom | 34590/76 |
| Sep. 1, 1976 | [GB] | United Kingdom | 36152/76 |
| Nov. 16, 1976 | [GB] | United Kingdom | 47667/76 |
| Feb. 8, 1977 | [GB] | United Kingdom | 5139/77 |
| Jun. 2, 1977 | [GB] | United Kingdom | 23443/77 |

[51] Int. Cl.³ .............. A01N 43/50; A01N 43/64; A01N 55/02; G07D 249/08
[52] U.S. Cl. ............................. 71/76; 71/92; 424/245; 424/269; 424/273 R; 548/101; 548/262; 548/336; 548/341
[58] Field of Search ............ 260/299, 308 R; 548/341, 262, 101; 424/269, 245, 273; 71/92, 76

[56] References Cited

U.S. PATENT DOCUMENTS

| | | | |
|---|---|---|---|
| 3,892,764 | 7/1975 | Metzger et al. | 548/341 |
| 4,005,083 | 1/1977 | Büchel et al. | 424/269 |
| 4,147,793 | 4/1979 | Shephard et al. | 424/269 |

FOREIGN PATENT DOCUMENTS

| | | | |
|---|---|---|---|
| 2407143 | 8/1975 | Fed. Rep. of Germany | 260/308 R |
| 2015913 | 4/1970 | France | 260/309 |
| 2249616 | 5/1975 | France | 541/341 |
| 2276302 | 1/1976 | France | 260/308 R |
| 754111 | 9/1976 | South Africa | 260/308 R |
| 1244530 | 9/1971 | United Kingdom | 548/341 |
| 1464224 | 6/1974 | United Kingdom | 548/262 |

*Primary Examiner*—Alton D. Rollins
*Attorney, Agent, or Firm*—Cushman, Darby & Cushman

[57] ABSTRACT

Triazoles of formula:

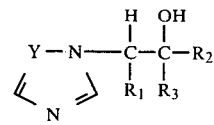

wherein $R_1$ is alkenyl, alkynyl or optionally substituted aralkyl; Y is =N—, $R_2$ is cycloalkyl, alkyl or haloalkyl, and $R_3$ is H, methyl or alkenyl, or esters, ethers, salts and metal complexes thereof. The triazoles have fungicidal and plant growth regulating activity.

55 Claims, No Drawings

FUNGICIDAL COMPOUNDS

This invention relates to heterocyclic compounds which are imidazole or 1,2,4-triazole compounds, to a process for preparing them, to compositions comprising them, to a method of combating fungal diseases in plants using them, and to a method of regulating the growth of plants using them.

The invention provides a compound of general formula (I):

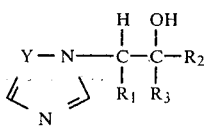

wherein $R_1$ is alkenyl, alkynyl or optionally substituted aralkyl, Y is =N— or =CH—, $R_2$ is cycloalkyl, alkyl or haloalkyl, and $R_3$ is hydrogen, methyl or alkenyl, or an ester, an ether, an acid addition salt or a metal complex thereof.

The compounds of the invention contain chiral centres. The compounds are generally obtained in the form of racemic mixtures. However these or other mixtures can be separated into the individual isomers by methods known in the art e.g. chromatography. In many cases, the compounds can be prepared stereospecifically in the form of a single diastereoisomer.

The alkyl groups, which can be straight or branched chain, preferably have 1 to 5 carbon atoms; examples are methyl, ethyl, propyl (n- or i-propyl) and butyl (n-, i- or t-butyl). Suitable alkenyl and alkynyl groups (which can also be straight or branched chain) are those having up to 7, preferably up to 4, carbon atoms; examples are allyl and propargyl.

The aralkyl group suitably contains 7 to 12 carbon atoms. The aralkyl (e.g. benzyl) group can be substituted in its alkyl (e.g. $CH_2$) and/or aryl (e.g. phenyl) moieties. Suitable substituents on its aryl (e.g. phenyl) moiety are halogen, $C_{1-4}$ alkyl [e.g. methyl, ethyl, propyl (n- or i-propyl) and butyl (n-, i- or t-butyl)], halo-($C_{1-4}$ alkyl), phenyl, halophenyl (e.g. chlorophenyl), cycloalkyl, nitro, cyano, $C_{1-4}$ alkoxy (e.g. methoxy or ethoxy), ($C_{1-4}$ alkylene)dioxy (e.g. methylenedioxy), ($C_{1-4}$ alkoxy) ($C_{1-4}$ alkyl) [e.g. 2-methoxy- or ethoxyethyl], mercapto, ($C_{1-4}$ alkyl) thio [e.g. methyl- or ethylthio], ($C_{1-4}$ alkyl) sulphonyl [e.g. methyl- or ethyl-sulphonyl], ($C_{1-4}$ halo-alkyl)sulphonyl [e.g. trifluoromethylsulphonyl], phenyl-sulphonyl, unsubstituted or mono- or di-($C_{1-4}$ alkyl) substituted sulphamoyl or carbamoyl, carboxy, ($C_{1-4}$ alkoxy)-carbonyl [e.g. methoxy- or ethoxy-carbonyl], unsubstituted or mono- or di-($C_{1-4}$ alkyl) substituted amino, ($C_{1-6}$ alkanoyl)amino, N-($C_{1-4}$ alkyl)-substituted ($C_{1-6}$ alkanoyl)-amino, formylamino, N-($C_{1-4}$ alkyl)-substituted formylamino, phenylethyl, phenoxy or benzyloxy. A suitable alkanoyl is acetyl or propionyl. The aralkyl group can have more than one ring substituent; examples of polysubstituted groups are those substituted with up to the maximum possible number (especially 1, 2 or 3) of for example halogen (particularly chlorine) atoms and/or nitro, methyl or methoxy groups. Suitable substituents on the alkyl moiety of the aralkyl (e.g. benzyl) group are halogen, $C_{1-4}$ alkyl (e.g. methyl), phenyl or benzyl, both latter groups being optionally substituted as indicated above for aryl, cyano, ($C_{1-4}$ alkoxy)carbonyl [e.g. methoxy- or ethoxy-carbonyl] or trihalomethyl (e.g. trifluoromethyl).

Examples of suitable aralkyl groups are benzyl itself, α-methylbenzyl, α-methylchlorobenzyl (e.g. α-methyl-p-chlorobenzyl), α-methyldichlorobenzyl (e.g. α-methyl-2,4-dichlorobenzyl), α-methylfluorobenzyl [e.g. α-methyl-p-fluorobenzyl], chlorobenzyl (for example o-, m- or p-chloro-benzyl), dichlorobenzyl (e.g. 3,4- 2,4- or 2,6-dichlorobenzyl), trichlorobenzyl (e.g. 2,3,6- or 2,4,5-trichlorobenzyl), tetrachlorobenzyl, pentachlorobenzyl, bromobenzyl (e.g. o-, m- or p-bromobenzyl), dibromobenzyl (e.g. 2,4-dibromobenzyl), fluorobenzyl (e.g. o-, m- or p-fluorobenzyl), difluorobenzyl (e.g. 2,4-difluorobenzyl), pentafluorobenzyl, methylbenzyl (e.g. o-, m- or p-methylbenzyl), dimethylbenzyl (e.g. 2,5-dimethylbenzyl), cyanobenzyl (e.g. p-cyanobenzyl), nitro-benzyl (e.g. p-nitrobenzyl), (trifluoromethyl)benzyl [e.g. m-(trifluoromethyl)benzyl], methoxybenzyl (e.g. o-, m- or p-methoxybenzyl), chloronitrobenzyl (e.g. 3-nitro-4-chlorobenzyl), chlorofluorobenzyl (e.g. 2-chloro-4-fluorobenzyl), fluorobromobenzyl (e.g. 2-fluoro-4-bromo-benzyl), methoxybromobenzyl (e.g. 2-methoxy-5-bromobenzyl), phenylbenzyl (e.g. p-phenylbenzyl), phenylethyl (e.g. 2-phenylethyl) or naphthylmethyl.

The cycloalkyl group suitably has 3 to 6 carbon atoms; preferably it is cyclopropyl, cyclopentyl or cyclohexyl.

Preferably the haloalkyl group contains 1 to 3 halogen atoms; examples are 2-chloroethyl, trifluoromethyl or trichloromethyl.

The halogen can be fluorine, chlorine, bromine or iodine.

A preferred class of compounds are those wherein $R_1$ is benzyl, α-methylbenzyl, α-methylchlorobenzyl, α-methyldichlorobenzyl, α-methylfluorobenzyl, chlorobenzyl, dichlorobenzyl, trichlorobenzyl, tetrachlorobenzyl, penta-chlorobenzyl, bromobenzyl, dibromobenzyl, fluorobenzyl, difluorobenzyl, pentafluorobenzyl, methylbenzyl, dimethyl-benzyl, cyanobenzyl, nitrobenzyl, trifluoromethylbenzyl, methoxybenzyl, chloronitrobenzyl, chlorofluorobenzyl, fluorobromobenzyl, methoxybromobenzyl, phenylbenzyl, phenylethyl or naphthylmethyl, Y is =N-, $R_2$ is propyl or butyl and $R_3$ is hydrogen or methyl. Also preferred are the corresponding compounds wherein Y is =CH—.

Particularly preferred are those compounds wherein $R_1$ is allyl, benzyl, α-methyl-p-chlorobenzyl, α-methyl-2, 4-dichlorobenzyl, α-methyl-p-fluorobenzyl, o-, m- or p-chlorobenzyl, 2,4-, 3,4- or 2,6-dichlorobenzyl, 2,4,5-or 2,3,6-trichlorobenzyl, pentachlorobenzyl, m- or p-bromobenzyl, 2,4-dibromobenzyl, o-, m- or p-fluorobenzyl, 2,4-difluorobenzyl, o- or p-methylbenzyl, 2,5-dimethyl-benzyl, p-nitrobenzyl, m-(trifluoromethyl)-benzyl, o- or p-methoxybenzyl, 3-nitro-4-chlorobenzyl, 2-chloro-4-fluorobenzyl, 2-fluoro-4-bromobenzyl, or 2-methoxy-5-bromobenzyl, Y is =N—, $R_2$ is i-propyl or t-butyl, and $R_3$ is hydrogen or methyl. Also particularly preferred are those compounds wherein $R_1$ is benzyl, o-chlorobenzyl, 2,4-dichlorobenzyl, o- or p-fluorobenzyl, p-bromobenzyl, or 2-chloro-4-fluorobenzyl, Y is =CH—, $R_2$ is t-butyl and $R_3$ is hydrogen or methyl.

Suitable salts are salts with inorganic or organic acids, e.g. hydrochloric, nitric, sulphuric, toluenesulphonic, acetic or oxalic acid. The esters are suitably alkanoates (e.g. acetates) and the ethers are suitably alkyl (e.g. methyl or ethyl), aryl (e.g. phenyl) or aralkyl (e.g. benzyl) ethers.

The metal complex is suitably one including copper, zinc, manganese or iron. It preferably has the general formula:

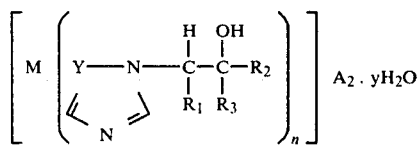

wherein Y, $R_1$, $R_2$ and $R_3$ are as defined above, M is a metal, A is an anion (e.g. a chloride, bromide, iodide, nitrate, sulphate or phosphate anion), n is 2 or 4, and y is 0 or an integer of 1 to 12.

Specific examples of the compounds are given in Table I.

TABLE 1

| NO | $R_1$ | $R_2$ | $R_3$ | Y | MELTING (OR BOILING) POINT °C. |
|---|---|---|---|---|---|
| 1* | p-Cl—C$_6$H$_4$CH$_2$— | t-Bu | H | =N— | 162–164° |
| 2 | C$_6$H$_5$CH$_2$— | t-Bu | H | =N— | 91–93° |
| 3 | p-F—C$_6$H$_4$CH$_2$— | t-Bu | H | =N— | 137–142° |
| 4 | p-F—C$_6$H$_4$CH$_2$— | t-Bu | Me | =N— | 152–153° |
| 5* | p-Cl—C$_6$H$_4$CH$_2$— | t-Bu | H | =N— | 133–134° |
| 6 | p-Cl—C$_6$H$_4$CH$_2$— | t-Bu | Me | =N— | 176–178° |
| 7 | p-Cl—C$_6$H$_4$CH$_2$— | t-Bu | H | =CH— | 179–181° |
| 8 | p-NO$_2$—C$_6$H$_4$CH$_2$ | t-Bu | H | =N— | 157–159° |
| 9 | 3,4-diCl—C$_6$H$_3$CH$_2$ | t-Bu | H | =N— | 186–188° |
| 10 | o-F—C$_6$H$_4$CH$_2$ | t-Bu | H | =N— | 100–102° |
| 11 | 2,4-diCl—C$_6$H$_3$CH$_2$ | t-Bu | H | =N— | 140–143° |
| 12 | CH$_2$CH=CH$_2$ | t-Bu | H | =N— | (110–120°/ 0.1mm) |
| 13 | m-CF$_3$—C$_6$H$_4$CH$_2$ | t-Bu | H | =N— | 71–73° |
| 14 | 3-NO$_2$-4-Cl—C$_6$H$_3$CH$_2$ | t-Bu | H | =N— | 177–178° |
| 15 | o-Cl—C$_6$H$_4$CH$_2$ | t-Bu | H | =N— | 100–102° |
| 16 | p-Br—C$_6$H$_4$CH$_2$ | t-Bu | H | =N— | 181–183° |
| 17 | m-F—C$_6$H$_4$CH$_2$ | t-Bu | H | =N— | 110–113° |
| 18 | m-Br—C$_6$H$_4$CH$_2$ | t-Bu | H | =N— | 133–136° |
| 19 | 2,4-diCl—C$_6$H$_3$CH$_2$ | i-Pr | H | =N— | 127–130° |
| 20 | p-Cl—C$_6$H$_4$CH$_2$ | i-Pr | H | =N— | 100–103° |
| 21+ | p-Cl—C$_6$H$_4$CH$_2$ | t-Bu | H | =N— | 138–140° |
| 22 | o-F—C$_6$H$_4$CH$_2$ | i-Pr | H | =N— | 74–78° |
| 23 | 2,6-diCl—C$_6$H$_3$CH$_2$ | t-Bu | H | =N— | 151–154° |
| 24 | 2-Cl,4-F—C$_6$H$_3$CH$_2$ | t-Bu | H | =N— | 137–140° |
| 25 | o-F—C$_6$H$_4$CH$_2$ | i-Pr | H | =N— | 122–127° |
| 26 | C$_6$Cl$_5$CH$_2$ | t-Bu | H | =N— | 173–175° |
| 27 | 2,4,5-triCl—C$_6$H$_2$CH$_2$ | t-Bu | H | =N— | 188–192° |
| 28 | 2,3,6-triCl—C$_6$H$_2$CH$_2$ | t-Bu | H | =N— | 168–172° |
| 29 | 2-Cl-4-F—C$_6$H$_3$CH$_2$ | t-Bu | H | =N— | 150–153° |
| 30 | 2-Cl-4-F—C$_6$H$_3$CH$_2$ | t-Bu | Me | =N— | 153–154° |
| 31 | 2,4-diF—C$_6$H$_3$CH$_2$ | t-Bu | H | =N— | 111–114° |
| 32 | p-F—C$_6$H$_4$CH(Me)— | t-Bu | H | =N— | 197–201° |
| 33° | 2,4-diCl—C$_6$H$_3$CH(Me) | t-Bu | H | =N— | 145–147° |
| 34 | p-Cl—C$_6$H$_4$CH(Me) | t-Bu | H | =N— | 182–185° |
| 35 | 2-F-4-Br—C$_6$H$_3$CH$_2$ | t-Bu | H | =N— | 171–174° |
| 36 | 2,4-diBr—C$_6$H$_3$CH$_2$ | t-Bu | H | =N— | 157–160° |
| 37 | o-MeO—C$_6$H$_4$CH$_2$ | t-Bu | H | =N— | 141–144° |
| 38 | o-Me—C$_6$H$_4$CH$_2$ | t-Bu | H | =N— | 123–125° |
| 39 | p-Me—C$_6$H$_4$CH$_2$ | t-Bu | H | =N— | 144–146° |
| 40 | 2,5-diMe—C$_6$H$_3$CH$_2$ | t-Bu | H | =N— | 114–117° |
| 41 | 2,4-diCl—C$_6$H$_3$CH$_2$ | t-Bu | H | =CH— | 191–193° |
| 42 | C$_6$H$_5$CH$_2$ | t-Bu | H | =CH— | 167–169° |
| 43 | 2-Cl-4-F—C$_6$H$_3$CH$_2$ | t-Bu | H | =CH— | 162–164° |
| 44 | o-Cl—C$_6$H$_4$CH$_2$ | t-Bu | H | =CH— | 167–169° |
| 45 | o-F—C$_6$H$_4$CH$_2$ | t-Bu | H | =CH— | 164–165° |
| 46 | p-F—C$_6$H$_4$CH$_2$ | t-Bu | H | =CH— | 164–166° |
| 47 | p-Br—C$_6$H$_4$CH$_2$ | t-Bu | H | =CH— | 199–201° |
| 48 | o-F—C$_6$H$_4$CH$_2$ | t-Bu | Me | =CH— | 146–149° |
| 49 | p-Br—C$_6$H$_4$CH$_2$ | t-Bu | Me | =CH— | 188–192° |
| 50 | m-Cl—C$_6$H$_4$CH$_2$ | t-Bu | H | =N— | 127–129° |
| 51 | p-MeO—C$_6$H$_4$CH$_2$ | t-Bu | H | =N— | |

TABLE 1-continued

| NO | R₁ | R₂ | R₃ | Y | MELTING (OR BOILING) POINT °C. |
|----|-----|-----|-----|-----|-----|
| 52 | 2-MeO-5Br—C₆H₃CH₂ | t-Bu | H | =N— | 184–186° |

*Compounds 1 and 5 are diastereoisomers of each other.
†This compound is in the form of a copper complex believed to have the structure

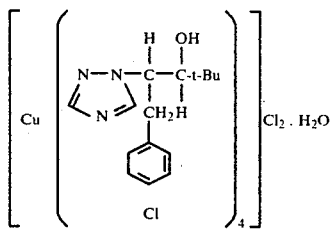

°Nuclear magnetic resonance studies have shown that Compounds 22, 24, 25 and 33 are each in the form of a mixture of stereoisomers. The weight ratios of the two isomers in each case are as follows:

| Compound | Weight |
|----------|--------|
| 22 | 9:1 |
| 24 | 7:1 |
| 25 | 4:1 |
| 33 | 1.5:1 |

The acetate of Compound 1 has also been prepared. This ester (Compound 53) has, in an impure form, a melting point of 125°–128° C.

The compounds of general formula (I) wherein $R_3$ is hydrogen, or a salt thereof, can be prepared by reducing, preferably at 0° to 100° C. and for 1 to 12 hours, a compound of general formula (II):

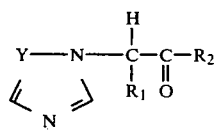

wherein Y, $R_1$ and $R_2$ are as defined above, or a salt thereof. Suitable reducing agents are sodium borohydride, lithium aluminium hydride or aluminium isopropoxide. If desired, catalytic hydrogenation using a suitable metal catalyst can be used. When the compound of general formula (II) is a sterically hindered ketone, a Grignard reagent, for example butylmagnesium halide (e.g. bromide or iodide) can be used as the reducing agent; when a reagent such as a butylmagnesium halide is used, single diastereoisomers are often produced.

The reduction can be performed by dissolving the reactants in a solvent such as diethyl ether or tetrahydrofuran (for lithium aluminium hydride reduction) or hydroxylic solvents (for sodium borohydride reduction). The reaction temperature will depend on the reactants and solvent; but generally the reaction mixture is heated under reflux. After the reaction, the product can be isolated by extraction into a convenient solvent after acidification with dilute mineral acid. On removal of the solvent in vacuo, the product may be crystallised from a convenient solvent.

The compounds of general formula (I) wherein $R_3$ is methyl or alkenyl, or a salt thereof, can be prepared by reacting, preferably at 15° to 80° C. and for 6 to 12 hours, a compound of general formula (II) or a salt thereof with the appropriate Grignard reagent e.g. a methyl or alkenyl magnesium halide such as methyl or allyl magnesium bromide or iodide. This reaction can be performed by methods known in the art.

The starting compound of general formula (II) may be made by reacting imidazole or 1,2,4-triazole, or a salt thereof, with a α-haloketone of general formula (III):

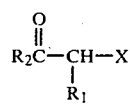

wherein X is halogen, preferably bromine or chlorine, and $R_1$ and $R_2$ are as defined above. This process may be carried out by heating the reactants together in the absence of a solvent or diluent, but preferably a solvent is present.

Suitable solvents are non-hydroxylic solvents such as acetonitrile, dimethylformamide, dimethyl sulfoxide, sulpholane and tetrahydrofuran. Hydroxylated solvents, for example, methanol and ethanol, may be used in certain circumstances when the presence of the hydroxyl group does not interfere with the reaction. The process can be carried out in the presence of a base such as sodium hydride, sodium ethoxide, excess imidazole or triazole, or an alkali metal carbonate (e.g. potassium carbonate). The reaction temperature will depend upon the choice of reactants, solvents and base, but generally the reaction mixture is heated under reflux. The process generally consists of dissolving the reactants in a solvent and then isolating the product by removal of the reactant solvent in vacuo. Unreacted imidazole or triazole can be removed by extraction of the product with a suitable solvent which is then washed with water. A crystallisation or other purification procedure may then be carried out if desired.

The α-halo ketones may be made by known methods.

The compounds of general formula (II) or a salt thereof may also be made by alkenylating, alkynylating or aralkylating a compound of general formula (IV);

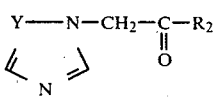

wherein Y and $R_2$ are as defined above. Further details of this reaction can be found in German Offenlegungsschrift No. 2610022, the disclosure of which document is incorporated herein by reference.

The salts, metal complexes, ethers and esters of the compounds of general formula (I) can be prepared from the latter in known manner. For example, the complexes can be made by reacting the uncomplexed compound with a metal salt in a suitable solvent.

The compounds are active fungicides, particularly against the diseases:

*Piricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants

*Plasmopara viticola* on vines

*Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines

*Cercospora arachidicola* on peanuts and other Cercospora species on for example sugar beet, bananas and soya beans

*Botrytis cinerea* (grey mould) on tomatoes, strawberries, vines and other hosts

*Phytophthora infestans* (blight) on tomatoes

*Venturia inaequalis* (scab) on apples

Some of the compounds have also shown a broad range of activities against fungi in vitro. They have activity against various post-harvest diseases on fruit (e.g. *Penicillium digatatum* and *italicum* on oranges and *Gloeosporium musarum* on bananas). Further some of the compounds are active as seed dressings against: Fusarium spp., Septoria spp., Tilletia spp. (i.e. bunt, a seed borne disease of wheat), Ustilago spp., and Pyrenophora spp. on cereals.

They can also be used as industrial (as opposed to agricultural) fungicides, e.g. as paint film fungicides.

The compounds also have plant growth regulating activities.

The plant growth regulating effects of the compounds are manifested as for example a stunting or dwarfing effect on the vegetative growth of woody and herbaceous mono- and di-cotyledonous plants. Such stunting or dwarfing may be useful, for example, in cereals and soya bean where reduction in stem growth may reduce the risk of lodging. Compounds which induce stunting or dwarfing may also be useful in modifying the growth of sugar cane thereby increasing the concentration of sugar in the cane at harvest. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum,* and *perenne, Agrostis tenuis, Cynodon dactylon* (Bermuda grass), *Dactylis glomerata,* Festuca spp. (e.g. *Festuca rubra*) and Poa spp. (e.g. *Poa pratense*). At least some of the compounds will stunt grasses without significant phytotoxic effects and without deleteriously affecting the appearance (particularly the colour) of the grass; this makes such compounds attractive for use on ornamental lawns and on grass verges. The compounds can also stunt weed species present in the grasses; examples of such weed species are sedges (e.g. Cyperus spp.) and dicotyledonous weeds. The growth of non-crop vegetation (e.g. weeds or cover vegetation) can be retarded thus assisting in the maintenance of plantation and field crops. The plant growth regulating effect may manifest itself in an increase in crop yield.

Other plant growth regulating effects caused by the compounds include alteration of leaf angle and promotion of tillering in monocotyledonous plants. The former effect may be useful for example in altering the leaf orientation of, for example, potato crops thereby letting more light into the crops and inducing an increase in phytosynthesis and tuber weight. By increasing tillering in monocotyledonous crops (e.g. rice), the number of flowering shoots per unit area may be increased thereby increasing the overall grain yield of such crops. The treatment of plants with the compounds of the invention can lead to the leaves developing a darker green colour.

Further the compounds may inhibit the flowering of sugar beet and thereby may increase sugar yield. They may also reduce the size of sugar beet without reducing significantly the sugar yield thereby enabling an increase in planting density to be made.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. However, on certain plants even application rates within these ranges may give undesired phytotoxic effects. Routine tests may be necessary to determine the best rate of application of a specific compound for any specific purpose for which it is suitable.

The compounds also have algicidal, anti-bacterial and anti-viral activities as well as herbicidal activity.

The compounds may be used as such for fungicidal or plant growth regulating purposes but are more conveniently formulated into compositions for such usage. The invention thus provides also a fungicidal or plant growth regulating composition comprising a compound of general formula (I) or a salt, complex, ether or ester thereof as hereinbefore defined, and a carrier or diluent.

The invention also provides a method of combating fungal diseases in a plant, which method comprises applying to the plant, to seed of the plant or to the locus of the plant or seed a compound or salt, complex, ether or ester thereof as hereinbefore defined.

It also provides a method of regulating the growth of a plant, which method comprises applying to the plant, to seed of the plant or to the locus of the plant or seed a compound or salt, complex, ether or ester thereof as hereinbefore defined.

The compounds, salts, complexes, ethers and esters can be applied in a number of ways, for example they can be formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butyoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound. The invention therefore also provides a fertiliser composition comprising the compound of general formula (I) or a salt, metal complex, ether or ester complex thereof.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or nonanionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity [e.g. other growth stimulating substances such as the gibberellins (e.g. $GA_3$, $GA_4$ or $GA_7$), the auxins (e.g. indoleacetic or indolebutyric acid) and the cytokinins (e.g. kinetin, diphenylurea, benzimidazole and benzyladenine) and other compounds having complementary fungicidal or insecticidal activity], as well as stabilising agent(s), for example epoxides (e.g. epichlorhydrin). The other fungicidal compound can be one which is capable of combating ear diseases of cereals (e.g. wheat) such as Septoria, Gibberella, Helminthosporium and the sooty mould complex; examples of such compounds are benomyl, carbendazole (BCM) and captafol.

Alternatively, it can be one which is capable of combating seed- and soil-borne diseases; examples of such compounds are Maneb and Captan.

The following Examples illustrate the invention; the temperatures are given in degrees Centigrade (°).

EXAMPLE 1

1-t-Butyl-2-(1,2,4-triazol-1-yl)-2-p-chlorobenzylethanol (Compound 1)

Stage I. 1,2,4-Triazole (33.4 g) and sodium ethoxide [from sodium (11.6 g) and ethanol (250 ml)] were refluxed for 1 hour. To this solution at the reflux temperature was added bromopinacolone (87 g), and heating was continued for a further 2 hours. The mixture was then cooled to ambient temperature, filtered to remove the precipitated sodium bromide and the solvent removed in vacuo. The residue was extracted with chloroform (100 ml). The solvent was washed with water (4×15 ml), dried (sodium sulphate) and filtered. Petroleum ether (b.p. 60°–80°) was added and the solution concentrated to yield α-1,2,4-triazol-4-yl-pinacolone, m.p. 176°. Further concentration of the solution gave α-1,2,4-triazol-1-yl-pinacolone, m.p. 63°–65°.

Stage II. α-1,2,4-Triazol-1-yl-pinacolone (3.3 g) in dimethyl formamide (20 ml) was added dropwise to a suspension of sodium hydride (0.48 g; 100%) in dimethyl formamide (10 ml) at room temperature with stirring. After stirring for two hours, p-chlorobenzyl chloride (3.2 g) in dimethyl formamide (2–3 ml) was added dropwise and the reaction mixture was kept at 5°–10° for two hours. The solvent was removed in vacuo and water was added to the residue. The aqueous solution was extracted with methylene chloride, the organic layer was washed with water and dried (magnesium sulphate), and the solvent was removed. Crystallisation of the yellow solid gave α-p-chlorobenzyl-α-1,2,4-triazol-1-yl-pinacolone, m.p. 122°–123° as a white crystalline solid.

Stage III. A solution of the product (2.0 g) of Stage II in methanol (20 ml) was treated portionwise with sodium borohydride (0.26 g). The reaction mixture was then refluxed for one hour. The solvent was removed in vacuo and hydrochloric acid (1 N; 40 ml) was added to the residue. The white precipitate was filtered off, washed with water, dried and crystallised from aqueous ethanol to give the title compound as a white crystalline solid, m.p. 162°–164°.

The starting material for Stage III can be obtained by the following alternative route.

Stage I. 4-Chlorobenzaldehyde (140.5 g) and pinacolone (100 g) in industrial methylated spirit (IMS; 200 ml) were added dropwise over 25 minutes to sodium hydroxide (40 g) in water (70 ml) and IMS (150 ml) with external cooling (ice/water) applied to maintain a temperature of not more than 25°. The resulting creamy suspension was stirred for a further 3 hours at 18° and was then filtered. The residue was washed with aqueous IMS and dried to give 4-chlorobenzal pinacolone, m.p. 83°–84°. The filtrate was concentrated under reduced pressure and allowed to stand for 2 days to give more of the chalcone product, m.p. 83°–84°.

Stage II. The chalcone (22.25 g) was suspended in ethyl acetate (125 ml) and Raney nickel (6 g) added after washing with ethyl acetate (4×15 ml). The apparatus was evacuated at the water pump and hydrogen was introduced to atmospheric pressure. The mixture was then shaken vigorously at room temperature. After 14.5 hours, hydrogenation ceased when the recorded uptake of gas was 2303 ml. The catalyst was filtered off, taking care not to allow the residue to become dry, and the filtrate concentrated in vacuo to afford crude 4-chlorobenzylpinacolone.

Stage III. 4-Chlorobenzylpinacolone (11.2 g) in carbon tetrachloride (80 ml) was cooled to about 5° and bromine (8 g) in carbon tetrachloride (20 ml) added dropwise at that temperature over 2 hours. Care was taken to keep free bromine to a minimum in the reaction mixture in order to avoid byproduct formation. The solution was washed with saturated aqueous sodium bicarbonate and with water, dried (magnesium sulphate), and concentrated in vacuo to afford, as a white crystalline solid, crude 1-(4'-chlorophenyl)-2-bromo-4,4-dimethylpentan-3-one, m.p. 48°–50°.

Stage IV. The product (0.69 g) of Stage III and 1,2,4-triazole (0.17 g) were mixed with potassium carbonate (0.52 g) in acetone (10 ml) and the mixture refluxed for 2 hours. After cooling to room temperature the inorganic material was filtered off and the filtrate concentrated in vacuo to afford crude α-p-chlorobenzyl-α-1,2,4-triazol-1-yl pinacolone.

EXAMPLE 2

1-t-Butyl-2-(1,2,4-triazol-1-yl)-2-benzylethanol (Compound 2)

Stage I. Pinacolone (10 g) in dry diethyl ether (30 ml) was added slowly to a suspension of sodamide (4.1 g) in dry diethyl ether (15 ml). The mixture was then stirred overnight at room temperature and then stirred and refluxed for 16 hours (the mixture was by this time orange-coloured). Benzyl chloride (13.2 g) was then added dropwise and the mixture refluxed for 24 hours. Water (100 ml) was added and the ethereal layer separated, and washed with water, dilute hydrochloric acid and again with water; it was then dried (sodium sulphate). The ether was evaporated under reduced pressure and then the residue was distilled to give α-benzylpinacolone, b.p. 78°–80°/0.06 mm Hg.

Stage II. Bromine (1.4 ml) was added dropwise to α-benzylpinacolone (5.2 g) in diethyl ether (80 ml) at about 10°. The solution was then stirred for 1 hour at room temperature and the ether was evaporated in vacuo to give a red liquid which was distilled in a bulb to give, as a slightly coloured liquid, α-bromo-α-benzyl pinacolone, b.p. 100°/0.1 mm Hg.

Stage III. 1,2,4-Triazole (0.28 g) in dimethyl formamide (5 ml) was added dropwise to a suspension of sodium hydride (0.1 g of 100%) in dimethyl formamide (2 ml). The reaction mixture was stirred for 2 hours and then α-bromo-α-benzyl pinacolone (1.0 g) in dimethylformamide (5 ml) was added. The reaction mixture was stirred at room temperature overnight and then poured into water (75 ml) to give, as a white crystalline solid, α-(1,2,4-triazol-1-yl)-α-benzyl pinacolone, m.p. 69°–71°.

Stage IV. α-1,2,4-Triazol-1-yl-α-benzylpinacolone (2.0 g) in methanol (20 ml) was treated portionwise with sodium borohydride (0.26 g). The mixture was then refluxed for one hour. The solvent was removed in vacuo and hydrochloric acid (1 N; 40 ml) was added to the residue. The white precipitate was filtered off, washed with water, dried and crystallised from aqueous ethanol to give the title compound as a white crystalline solid.

EXAMPLE 3

1-(1,2,4-Triazol-1-yl)-1-p-fluorobenzyl-2-t-butyl-propan-2-ol (Compound 4)

An ethereal solution of methylmagnesium iodide [prepared by reacting methyl iodide (6.2 g) with magnesium (1.1 g) in dry diethyl ether] was treated dropwise with α-1,2,4-triazol-1-yl-α-p-fluorobenzyl-pinacolone (4.0 g) in dry diethyl ether (30 ml). The mixture was then refluxed for one hour, cooled and treated with 10% sulphuric acid (20 ml). The insoluble material was filtered off, washed with dilute hydrochloric acid and water and then dried to give, after crystallisation from aqueous ethanol, the title compound.

EXAMPLE 4

1-t-Butyl-2-(1,2,4-triazol-1-yl)-2-p-chlorobenzylethanol (Compound 5)

A solution of butylmagnesium bromide [prepared from butyl bromide (5.63 g) and magnesium (1.0 g) in dry diethyl ether] was treacted dropwise with α-(1,2,4-triazol-1-yl)-α-p-chlorobenzylchloride (4.0 g) in diethyl ether (30 ml) and the mixture was refluxed for one hour. The reaction mixture was treated with dilute sulphuric acid (20 ml) and the ethereal layer was separated, washed with water and dried (sodium sulphate). Removal of solvent in vacuo gave a white solid which was crystallised from diethyl ether/petrol (60°-80°) to give the title compound.

EXAMPLE 5

The copper complex of Compound 1. (Compound 21)

Cupric chloride (0.9 g; 0.005 mole) dissolved in water (4 ml) was added dropwise to a solution of Compound 1 (2.9 g; 0.01 mole) in ethanol (60 ml) and the resulting green solution stirred for half an hour. The volume of solvent was then reduced by about 30 ml and water (30 ml) added. A green oil separated out. The aqueous phase was decanted off and the organic phase was stirred for 30 minutes with iso-propanol (50 ml). The resultant green solid was then filtered off and dried to give, after recrystallisation from ethanol/water, the copper complex (1.6 g).

EXAMPLE 6

This Example lists a number of compositions of the invention.

| (1) Dispersible Powder | |
|---|---|
| Compound 1 | 50% wt/wt |
| Aerosol OT | 2% |
| Polyfon H | 5% |
| China Clay | 43% |
| (2) Emulsifiable Concentrate | |
| Compound 1 | 100 g/liter |
| Amine dodecylbenzene sulphonate | 400 g/liter |
| 2-n-Butoxyethanol | to 1 liter |
| (3) Aqueous Suspension | |
| Compound 1 | 250 g/liter |
| Polyfon H | 25 g/liter |
| Bentonite | 15 |
| Polysaccharide | 0.75 |
| Water | to 1 liter |
| (4) Dust | |
| Compound 1 | 5% wt/wt |
| China clay | 95% |
| (5) Granules | |
| Compound 1 | 5% wt/wt |
| Starch | 5% |
| China clay | 90% |
| (6) Solvent solution | |
| Compound 1 | 200 g/liter |
| Dimethylformamide | to 1 liter |

EXAMPLE 7

The compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots.

The test compounds were formulated either by bead-milling with aqueous Dispersol T or as a solution in acetone/ethanol which was diluted to the required concentration immediately before use. For the foliage diseases, 100 p.p.m. a.i. suspensions were sprayed on to the foilage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil (roots) and to the foliage (by spraying) one or two days before the plant was inoculated with the diseases. An exception was the test on *Erysiphe graminis*, in which the plants were inoculated 24 hours before treatment. After inoculation, the plants were put into an appropriate environment to allow infection to take place and then incubated until the disease was ready for assessment. The period between inoculation and assessment varied from 4 to 14 days according to the disease and environment.

The disease control was recorded by the following grading:
4 = No disease
3 = 0-5%
2 = 6-25%
1 = 26-60%
0 = >60%

The results are shown in Table II.

TABLE II

| COMPOUND NO | DISEASE CONTROL | | | | | | |
|---|---|---|---|---|---|---|---|
| | *Puccinia recondita* in wheat | *Phytophthora infestans* in tomato | *Plasmopara viticola* in vines | *Piricularia oryzae* in rice | *Cercospora arachidicola* in peanuts | *Botrytis cinerea* in tomato | *Erysiphe graminis* in barley |
| 1 | 4+ | 0 | 3 | 4 | | 3 | 4 |
| 2 | 4 | 0 | 0 | 1-2 | | 3 | 4 |
| 3 | 4 | 0 | 0 | 3 | | 1-2 | 4 |
| 4 | 4 | 0 | 0 | 3 | | 0 | 4 |
| 5 | 4+ | 0 | 3-4 | 0-1 | | 3 | 4 |
| 6 | 2 | 0 | 3 | 0 | | 1-2 | 4 |
| 7 | 4 | 0 | 0 | 0 | | 3-4 | 4 |
| 8 | 4 | 0 | 0-1 | 0 | | 0-2 | 4 |
| 9 | 4 | 0 | 0 | 0 | | 0-1 | 4 |
| 10 | 4 | 0 | 2-3 | 2-3 | | 0-2 | 4 |
| 11* | 4 | 0 | 0-1 | 1 | | 2-3 | 4 |
| 12 | 4 | 0 | 0-3 | 1 | | 0 | 4 |
| 13 | 4 | 0 | 0 | 1-2 | | 0 | 4 |
| 14 | 2 | 0 | | 0 | | 1-2 | 4 |
| 15 | 4 | 0 | — | 3 | | 3 | 4 |
| 16 | 4 | 0 | 0 | 3 | | 4 | 4 |
| 17 | 3 | 4 | P | P | | 0 | 3 |
| 18 | 3 | 0 | — | 0 | | 1-2 | 4 |

TABLE II-continued

| COMPOUND NO | DISEASE CONTROL | | | | | | |
|---|---|---|---|---|---|---|---|
| | Puccinia recondita in wheat | Phytophthora infestans in tomato | Plasmopara viticola in vines | Piricularia oryzae in rice | Cercospora arachidicola in peanuts | Botrytis cinerea in tomato | Erysiphe graminis in barley |
| 19 | 1 | 0 | 0 | 0 | | 2-3 | 0 |
| 20 | 1 | 0 | 0 | 0 | | 2-3 | |
| 21 | 3 | 3-4 | 3 | | | 3 | 4 |
| 22 | 4 | 0 | 0 | 1 | | 0 | 4 |
| 23 | 4 | 0 | 0 | 2-3 | | 1-2 | 4 |
| 24 | 4 | 0 | 0 | 2-3 | | 1-2 | 3 |
| 25 | 3 | 0 | 0 | 1 | | 0-1 | 4 |
| 26 | 0-1 | 0 | 0 | 2 | | 0-1 | 3-4 |
| 27 | 0-1 | 0 | 0 | 0 | | 2-3 | 3-4 |
| 28 | 3 | 0 | 0 | 0-1 | | 2-3 | 4 |
| 29 | 4 | 1-3 | 0 | 0-1 | | 2-3 | 3 |
| 30 | 1-2 | 2-3 | 0 | 0 | | 1-2 | 3 |
| 31 | 3 | 0 | 4 | 3 | 3 | 2 | 2-3 |
| 32 | 4 | 0 | 0-1 | 0-1 | 3-4 | 3 | 4 |
| 33 | 4 | 0 | 0 | 0 | 1-2 | 2 | 4 |
| 34 | 3-4 | 0 | 0 | 0 | 2 | 2-3 | 4 |
| 35 | 4 | 0 | 0 | 0 | 3 | 1-2 | 3 |
| 36 | 4 | 0 | 0 | 0-1 | 0 | 0-1 | 4 |
| 37 | 4 | 0 | 0 | 1-2 | 3-4 | 3 | 4 |
| 38 | 3 | 0 | 0 | 0 | 4 | 3-4 | 4 |
| 39 | 3 | 0 | 0 | 0 | 4 | 3-4 | 4 |
| 40 | 4 | 0 | 0 | 1 | | 0 | 4 |
| 41 | 1-2 | 0 | 0 | 0-1 | | 1-2 | 4 |
| 42 | 3 | 0 | 0 | 0 | | 0 | 4 |
| 43 | 3 | 0-1 | 0 | 0-1 | | 0 | 4 |
| 44 | | 1 | 0 | 0-1 | | 1 | 4 |
| 45 | | 0 | 0 | 0 | | 2-3 | 4 |
| 46 | 3 | 0 | 0 | 0-1 | 0 | 2 | 4 |
| 47 | 3 | 0 | 0 | 0 | 0 | 3 | 4 |
| 48 | 0-1 | 0-1 | | 0 | | 3 | 4-3 |
| 49 | 0-3 | 0 | | 0 | | 3-4 | 4-3 |
| 50 | | 1 | | | | 1-2 | 0 |
| 51 | | | | | | | |
| 52 | | | | | | | |
| 53 | | | | | | | |

*This compound is of interest because it has a weaker stunting effect on vegetative growth of monocotyledonous plants (e.g. wheat and barley) than the mono (chloro- and fluoro-) compounds.
†At lower concentrations, Compound 1 is more active than its diastereoisomer Compound 5.
P = Compound phytotoxic.

EXAMPLE 8

This Example illustrates the protectant activity (at 50 ppm) of the compounds against various fruit fungal diseases.

The activity of the compounds against apple powdery mildew (*Podosphaera leucotricha*) and vine powdery mildew (*Uncinula necator*) was determined as follows.

Small apple (Jonathan) and vine plants about 3 weeks old and growing in mini pots (diameter: 3 cm) were sprayed first with the solution or suspension of the test compound, allowed to dry overnight in a growth room and then infected on the following day with spores of the disease by placing them in an enclosed space and allowing spores of the disease blown into the still space to settle upon them over four to six hours.

Assessment was made of the percentage amount of disease on the leaves of the plants (after 8 days for apples and 9 to 10 days for vines).

The tests against apple scab (*Venturia inaequalis*) were performed as follows.

*Venturia inaequalis* was treated as an obligate parasite, the spores of the fungus being transferred from plant to plant by-passing agar plate culture which ensures a very pathogenic fungus.

Infected leaves were removed from stock plants 13 days after inoculation. The spores were removed from the leaves by agitation in a small volume of deionised water, counted and then adjusted to 100,000 spores/ml. This suspension was sprayed onto the undersides of apple seedling leaves of one of three susceptible varieties, i.e. Jonathan, Granny Smith and Red Delicious. The inoculated seedlings were immediately placed in a high humidity cabinet at 19° C. and left therein for 48 hours. After this incubation period the plants were placed in growth room conducive to disease development. The disease was easily assessed 12 or 13 days after inoculation.

The test compound was applied 24 hours after inoculation.

The grading system used is the same as for Table II. Table III shows the results.

TABLE III

| COMPOUND NO | DISEASE CONTROL | | |
|---|---|---|---|
| | Podosphaera leuchotricha on apples | Uncinula necator on vines | Venturia inaequalis on apples |
| 1 | 4 | 3 | 3 |
| 2 | 4 | 4 | 0-4 |
| 3 | 4 | 4 | 0 |
| 4 | 0 | 4 | |
| 5 | 4 | 4 | 0 |
| 6 | 0 | 2 | |
| 7 | 0 | 1 | 0 |
| 8 | 4 | 4 | |
| 9 | 0 | 4 | 0 |
| 10 | 1 | 0 | 0 |
| 11 | 3 | 4 | 0-2 |
| 12 | 0 | 0 | 0 |
| 13 | 0 | 1 | 0 |
| 14 | 0 | 0 | |

TABLE III-continued

| COMPOUND NO | DISEASE CONTROL | | |
|---|---|---|---|
| | Podosphaera leuchotricha on apples | Uncinula necator on vines | Venturia inaequalis on apples |
| 15 | 1 | 0 | |
| 16 | 2 | 4 | 4 |
| 17 | 2 | 4 | 0 |
| 18 | 0 | 4 | |
| 19 | 2 | 4 | 1 |
| 20 | 0 | 4 | 0 |
| 21 | 4 | 4 | 2 |
| 22 | 1 | 2 | 0 |
| 23 | 0 | 4 | 0 |
| 24 | 2 | 4 | 1 |
| 25 | 0 | 2 | 0 |
| 26 | | | |
| 27 | 0 | 1 | 0 |
| 28 | 0 | 3 | 1 |
| 29 | 4 | 4 | 4 |
| 30 | 1 | 0 | 0 |
| 31 | 2 | 4 | 2 |
| 32 | 4 | 4 | 1 |
| 33 | 4 | 4 | 4 |
| 34 | 4 | 4 | 4 |
| 35 | | | |
| 36 | 3 | 4 | 2 |
| 37 | 2 | 1 | 1 |
| 38 | 4 | 4 | 3 |
| 39 | 4 | 4 | 4 |
| 40 | 0 | 2 | 0 |
| 41 | 0 | 0 | |
| 42 | 0 | 1 | 0 |
| 43 | 1 | 1 | 0 |

EXAMPLE 9

The compounds were tested at 50 ppm and as a protectant dip against *Penicillium digitatum* on oranges and *Gloeosporium musarum* on bananas.

The oranges were scrubbed and then wiped over with industrial methylated spirit. The peel was then removed and cut into discs with a No. 6 cork borer. The peel discs were then dipped into a solution (containing 0.1% Tween 20 as a wetting agent) of the test compound. They were then put outer side uppermost in Repli dishes. The discs were allowed to dry and were then sprayed with a spore suspension of *Penicillium digitatum* at a concentration of $1 \times 10^6$ spores/ml. The dishes were then stored in a moist environment at 19° C. for 13 days.

The tests on bananas were performed in a similar fashion using discs of banana peel.

The discs were then assessed using the grading system used for Table II. Table IV shows the results.

TABLE IV

| COMPOUND NO | DISEASE CONTROL | |
|---|---|---|
| | P. digitatum on oranges | G. musarum on bananas |
| 1 | 4 | 4 |
| 2 | 4 | 0 |
| 3 | 1 | 3 |
| 4 | | |
| 5 | 1 | 2 |
| 6 | | |
| 7 | | |
| 8 | | |
| 9 | | |
| 10 | 3 | 3 |
| 11 | 1 | 1 |
| 12 | | |
| 13 | 0 | 1 |
| 14 | | |
| 15 | 0 | 4 |
| 16 | 4 | 0 |
| 17 | | |
| 18 | | |
| 19 | | |
| 20 | | |
| 21 | 4 | |
| 22 | | |
| 23 | | |
| 24 | | 1 |
| 25 | | |
| 26 | | |
| 27 | | |
| 28 | | |
| 29 | 4 | 2-4 |
| 30 | | |
| 31 | | 4 |
| 32 | | |

EXAMPLE 10

This Example illustrates the plant growth regulating properties of the compounds. The compounds were applied in the form of a 5000 p.p.m. solution in distilled water and the solution was then applied to the foliage of young seedlings of wheat, barley, maize, rice, Lolium rye grass, soya, cotton, groundnut, lettuce, tomato, Mung bean and French bean. The experiments were replicated twice. After 21 days from treatment, the plants were assessed for plant growth regulating effects and phytotoxic symptoms.

Table V shows the stunting effect of the compounds on the vegetative growth using the following grading:
0 = ≦20% retardation
1 = 21–40% retardation
2 = 41–60% retardation
3 = 61–80% retardation
If no figure is given, the compound was substantially inactive as a stunting agent.

Additional plant growth regulating properties are indicated as follows:
G = darker green leaf colour
A = apical effect
T = tillering effect The symbol "—" is used to indicate that the compound has not been tested on that particular crop.

The asterisk (*) indicates that the compound was applied at 4000 p.p.m.

TABLE V

| COMPOUND | WHEAT | BARLEY | MAIZE | RICE | LOLIUM RYE GRASS | SOYA | COTTON | GROUND NUT | LETTUCE | TOMATO | MUNG BEAN | FRENCH BEAN |
|---|---|---|---|---|---|---|---|---|---|---|---|---|
| 1 | 1G | 1G | | 0 | G | 1GA | 0 | 1 | 2G | 1G | 1A | GA |
| 2 | 1 | 2G | | 0 | G | 1GA | 0 | 3 | 2G | 2GAT | 2GA | 1GA |
| 3 | 2G | 3G | | 1 | 1G | 1G | 1 | 3 | 3GA | 2GA | 1GA | 1GA |
| 4 | | | | | | | | | | | | |
| 5 | 1G | 1G | | 0 | G | 1G | 1 | 3 | 3GA | 2A | 2A | 1GA |
| 6 | | | | | | 2GA | 1 | — | A | 0 | 1A | |

TABLE V-continued

| COMPOUND | WHEAT | BARLEY | MAIZE | RICE | LOLIUM RYE GRASS | SOYA | COTTON | GROUND NUT | LETTUCE | TOMATO | MUNG BEAN | FRENCH BEAN |
|---|---|---|---|---|---|---|---|---|---|---|---|---|
| 7 | — | — | — | — | — | — | — | — | — | — | — | — |
| 8 | 1G | 1G | | 0 | 0 | 1GA | G | | GA | | A | 2A |
| 9 | | | | | | 1GA | G | | GA | | | 2G |
| 10 | 1GT | | | | G | 2A | 1G | | A | O | | 2GA |
| 11 | | | | | | 2GA | 2 | | GA | | | 1GA |
| 12 | | | | | — | 1GA | | | 1GA | 2G | 2 | 2GA |
| 13 | 1 | 0 | | | 2 | 2GA | G | | A | GA | | 2A |
| 14 | | | | | | 1GA | 0 | | | | | GA |
| 15 | | | | | 0 | 1GA | 1G | | GA | GA | A | 1GA |
| 16 | 1G | 1G | | 0 | 1G | 2GA | G | | GA | G | A | 3GA |
| 17 | 1G | 1 | | 0 | 0 | 2GAT | 1G | | | G | A | 3A |
| 18 | | | | | | | | | | | | |
| 19 | 1 | 1 | | | — | | | | 2A | 2 | | — |
| 20 | 2 | 2 | 1 | | — | 2GA | | | 2GA | 3A | — | 2G |
| 21 | 0 | 0 | | | G | 1GAT | | T | GA | | | 1GA |
| 22* | | | | | — | | | | | | | — |
| 23* | | | | | — | 3G | 1GA | | 1 | 3GA | — | 3GA |
| 24* | 2T | 1 | 1G | | — | 3GA | A | | 1A | 3GA | — | 3GA |
| 25* | | | | | — | 3GA | | | 2A | 3GA | — | |
| 26* | | | | | — | | | | | | | — |
| 27* | | | | | — | | | | | | | — |
| 28* | 2 | | 1G | | — | | | | 2A | 3GA | — | |
| 29* | 2T | 2 | 2 | 1 | — | 3A | 3 | | 3GA | 3 | — | 3GA |
| 30* | | | | | — | 2GA | 2A | | A | 2G | — | |
| 31 | — | — | — | — | — | — | — | — | — | — | — | — |
| 32* | | | | | — | | | | | | — | |
| 33 | — | — | — | — | — | — | — | — | — | — | — | — |
| 34* | | | | | — | | | | | | | — |
| 35* | 2GT | 2G | | 1 | — | 3GA | 1 | | | 2G | — | 2GA |
| 36 | | | | | | | | | | | | |
| 37* | | | | | — | | | | | | — | |
| 38* | 2GT | 2GT | | | — | 3GA | | | 1A | 2G | — | 3GA |
| 39* | | 2 | | 1 | | 2 | 1A | | 1A | 1 | — | 1G |
| 40 | | | | | | | | | | | | |
| 41* | | | | | — | | | | | | | — |

We claim:
1. A compound having plant fungicidal and/or plant growth regulating activity and the formula

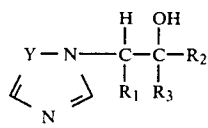

wherein Y is =N—, $R_1$ is allyl or is benzyl optionally ring substituted with one or two substituents selected from the class consisting of halogen, $C_{1-4}$ alkyl, halo ($C_{1-4}$ alkyl), $C_{3-6}$ cycloalkyl, nitro, cyano, $C_{1-4}$ alkoxy and ($C_{1-4}$ alkylene)dioxy, and/or optionally substituted on the α-carbon atom with one $C_{1-4}$ alkyl, $R_2$ is propyl or butyl and $R_3$ is hydrogen or methyl; or an alkanoate ester, an acid addition salt or a copper, zinc, manganese or iron complex thereof.

2. A compound as claimed in claim 1 wherein $R_1$ is allyl, benzyl, α-methylbenzyl, α-methylchlorobenzyl, α-methyldichloro-benzyl, α-methylfluorobenzyl, chlorobenzyl, dichloro-benzyl, bromobenzyl, dibromobenzyl, fluorobenzyl, difluorobenzyl, methylbenzyl, dimethylbenzyl, cyanobenzyl, nitrobenzyl, trifluoromethylbenzyl, methoxybenzyl, chloronitrobenzyl, chlorofluorobenzyl, fluorobromobenzyl, methoxybromobenzyl or phenylbenzyl and $R_2$ is i-propyl or t-butyl.

3. A compound as claimed in claim 2 wherein $R_1$ is allyl, benzyl, α-methyl-p-chlorobenzyl, α-methyl-2,4-dichlorobenzyl, α-methyl-p-fluorobenzyl, o-, m- or p-chlorobenzyl, 2,4-, 3,4- or 2,6-dichlorobenzyl, m- or p-bromobenzyl, 2,4-dibromobenzyl, o-, m- or p-fluorobenzyl, 2,4-difluorobenzyl, o- or p-methylbenzyl, 2,5-dimethylbenzyl, p-nitrobenzyl, m-(trifluoromethyl)benzyl, o- or p-methoxybenzyl, 3-nitro-4-chlorobenzyl, 2-chloro-4-fluorobenzyl, 2-fluoro-4-bromobenzyl or 2-methoxy-5-bromobenzyl.

4. A compound as claimed in claim 1 which is in the form of a copper complex.

5. A compound as claimed in claim 1 which is 1-t-butyl-2-(1,2,4-triazol-1-yl)-2-benzylethanol.

6. A compound as claimed in claim 1 which is 1-t-butyl-2-(1,2,4-triazol-1-yl)-2-p-fluorobenzyl-ethanol.

7. A compound as claimed in claim 1 which is 1-t-butyl-2-(1,2,4-triazol-1-yl)-2-(2′,4′dichloro-benzyl)ethanol.

8. A compound as claimed in claim 1 which is 1-t-butyl-2-(1,2,4-triazol-1-yl)-2-p-bromobenzyl-ethanol.

9. A compound as claimed in claim 1 which is 1-t-butyl-2-(1,2,4-triazol-1-yl)-2-(2′-chloro-4′-fluorobenzyl)ethanol.

10. A compound as claimed in claim 1 which is 1-t-butyl-2-(1,2,4-triazol-1-yl)-2-o-methoxybenzyl-ethanol.

11. A compound as claimed in claim 1 which is 1-t-butyl-2-(1,2,4-triazol-1-yl)-2-o-methylbenzyl-ethanol.

12. A compound as claimed in claim 1 which is 1-t-butyl-2-(1,2,4-triazol-1-yl)-2-p-methylbenzyl-ethanol.

13. A compound as claimed in claim 1 which is a diastereoisomer of 1-t-butyl-2-(1,2,4-triazol-1-yl)-2-p-chloro-benzyl-ethanol, said diastereoisomer having a melting point of 162°–164° C. or a copper complex thereof.

14. A compound as claimed in claim 1 which is a diastereoisomer of 1-t-butyl-2-(1,2,4-triazol-1-yl)-2-p-chloro-benzyl-ethanol, said diastereoisomer having a melting point of 133°–134° C.

15. A fungicidal or plant growth regulating composition consisting essentially of a fungicidally or plant growth regulating effective amount of a compound, ester, salt or metal complex as claimed in claim 1 and a carrier.

16. A fungicidal or plant growth regulating composition consisting essentially of a fungicidally or plant growth regulating effective amount of a compound as claimed in claim 2 and a carrier.

17. A fungicidal or plant growth regulating composition consisting essentially of a fungicidally or plant growth regulating effective amount of a compound as claimed in claim 3 and a carrier.

18. A fungicidal or plant growth regulating composition consisting essentially of a fungicidally or plant growth regulating effective amount of a compound as claimed in claim 13 and a carrier.

19. A fungicidal or plant growth regulating composition consisting essentially of a fungicidally or plant growth regulating effective amount of a compound as claimed in claim 14 and a carrier.

20. A fungicidal or plant growth regulating composition consisting essentially of a fungicidally or plant growth regulating effective amount of a metal complex as claimed in claim 4 and a carrier.

21. A fungicidal or plant growth regulating composition consisting essentially of a fungicidally or plant growth regulating effective amount of a compound as claimed in claim 5 and a carrier.

22. A fungicidal or plant growth regulating composition consisting essentially of a fungicidally or plant growth regulating effective amount of a compound as claimed in claim 6 and a carrier.

23. A fungicidal or plant growth regulating composition consisting essentially of a fungicidally or plant growth regulating effective amount of a compound as claimed in claim 7 and a carrier.

24. A fungicidal or plant growth regulating composition consisting essentially of a fungicidally or plant growth regulating effective amount of a compound as claimed in claim 8 and a carrier.

25. A fungicidal or plant growth regulating composition consisting essentially of a fungicidally or plant growth regulating effective amount of a compound as claimed in claim 9 and a carrier.

26. A fungicidal or plant growth regulating composition consisting essentially of a fungicidally or plant growth regulating effective amount of a compound as claimed in claim 10 and a carrier.

27. A fungicidal or plant growth regulating composition consisting essentially of a fungicidally or plant growth regulating effective amount of a compound as claimed in claim 11 and a carrier.

28. A fungicidal or plant growth regulating composition consisting essentially of a fungicidally or plant growth regulating effective amount of a compound as claimed in claim 12 and a carrier.

29. A method of combating fungal diseases in, or regulating the growth of, a plant, the method consisting essentially of applying to the plant, to seed of the plant or to the locus of the plant or seed, a fungicidally or plant growth regulating effective amount of a compound, ester, salt or metal complex as claimed in claim 1.

30. A method of combating fungal diseases in, or regulating the growth of, a plant, the method consisting essentially of applying to the plant, to seed of the plant or to the locus of the plant or seed, a fungicidally or plant growth regulating effective amount of a compound as claimed in claim 2.

31. A method of combating fungal diseases in, or regulating the growth of, a plant, the method consisting essentially, of applying to the plant, to seed of the plant or to the locus of the plant or seed, a fungicidally or plant growth regulating effective amount of a compund as claimed in claim 3.

32. A method of combating fungal diseases in, or regulating the growth of, a plant, the method consisting essentially of applying to the plant, to seed of the plant or to the locus of the plant or seed, a fungicidally or plant growth regulating effective amount of a compound as claimed in claim 13.

33. A method of combating fungal diseases in, or regulating the growth of, a plant, the method consisting essentially of applying to the plant, to seed of the plant or to the locus of the plant or seed, a fungicidally or plant growth regulating effective amount of a compound as claimed in claim 14.

34. A method of combating fungal diseases in, or regulating the growth of, a plant, the method consisting essentially of applying to the plant, to seed of the plant or to the locus of the plant or seed, a fungicidally or plant growth regulating effective amount of a metal complex as claimed in claim 4.

35. A method of combating fungal diseases in, or regulating the growth of, a plant, the method consisting essentially of applying to the plant, to seed of the plant or to the locus of the plant or seed, a fungicidally or plant growth regulating effective amount of a compound as claimed in claim 5.

36. A method of combating fungal diseases in, or regulating the growth of, a plant, the method consisting essentially of applying to the plant, to seed of the plnat or to the locus of the plant or seed, a fungicidally or plant growth regulating effective amount of a compound as claimed in claim 6.

37. A method of combating fungal diseases in, or regulating the growth of, a plant, the method consisting essentially of applying to the plant, to seed of the plant or to the locus of the plant or seed, a fungicidally or plant growth regulating effective amount of a compound as claimed in claim 7.

38. A method of combating fungal diseases in, or regulating the growth of, a plant, the method consisting essentially of applying to the plant, to seed of the plant or to the locus of the plant or seed, a fungicidally or plant growth regulating effective amount of a compound as claimed in claim 8.

39. A method of combating fungal diseases in, or regulating the growth of, a plant, the method consisting essentially of applying to the plant, to seed of the plant or to the locus of the plant or seed, a fungicidally or plant growth regulating effective amount of a compound as claimed in claim 9.

40. A method of combating fungal diseases in, or regulating the growth of, a plant, the method consisting essentially of applying to the plant, to seed of the plant or to the locus of the plant or seed, a fungicidally or plant growth regulating effective amount of a compound as claimed in claim 10.

41. A method of combating fungal diseases in, or regulating the growth of, a plant, the method consisting essentially of applying to the plant, to seed of the plant or to the locus of the plant or seed, a fungicidally or plant growth regulating effective amount of a compound as claimed in claim 11.

42. A method of combating fungal diseases in, or regulating the growth of, a plant, the method consisting essentially of applying to the plant, to seed of the plant or to the locus of the plant or seed, a fungicidally or plant growth regulating effective amount of a compound as claimed in claim 8.

43. A compound having the formula

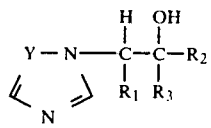

wherein Y is —N—, $R_1$ is allyl or is benzyl optionally ring substituted with one or two substituents selected from the class consisting of halogen, methyl, ethyl, trifluoromethyl, nitro, cyano, methoxy and ethoxy, and/or optionally substituted on the α-carbon atom with one methyl, $R_2$ is i-propyl, i-butyl or t-butyl and $R_3$ is hydrogen or methyl; or an acetate ester, an acid addition salt or a copper, zinc, manganese or iron complex thereof.

44. A method of stunting the growth of a grass, the method consisting essentially of applying to the grass, to seed of the grass or to the locus of the grass or seed, and in an amount sufficient to stunt the growth of the grass, a compound of formula:

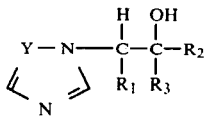

wherein Y is =N—, $R_1$ is benzyl optionally substituted with one or two substituents selected from the class consisting of halogen, $C_{1-4}$ alkyl and nitro, $R_2$ is butyl and $R_3$ hydrogen; or an alkanoate ester, an acid addition salt or a copper, zinc, manganese or iron complex thereof.

45. A method as claimed in claim 44 wherein the compound applied is one wherein $R_1$ is benzyl; p-chlorobenzyl, p-fluorobenzyl, p-bromobenzyl, m-fluorobenzyl, p-nitrobenzyl, 4-fluoro-2-chlorobenzyl, 2-fluoro-4-bromobenzyl and 2,4-difluorobenzyl, and $R_2$ is t-butyl.

46. A method as claimed in claim 44 wherein the compound applied is a diastereoisomer of 1-t-butyl-2-(1,2,4-triazol-1-yl)-2-p-chloro-benzylethanol, said diastereoisomer having a melting point of 162°–164° C. or a copper complex thereof.

47. The method as claimed in claim 44 wherein the compound applied is a diastereoisomer of 1-t-butyl-2-(1,2,4-triazol-1-yl)-2-p-chloro-benzylethanol, said diastereoisomer having a melting point of 133°–134° C.

48. A method as claimed in claim 46 wherein the metal complex applied is a copper complex of 1-t-butyl-2-(1,2,4-triazol-1-yl)-2-p-chloro-benzylethanol.

49. A method as claimed in claim 44 wherein the compound applied is 1-t-butyl-2-(1,2,4-triazol-1-yl)-2-benzylethanol.

50. A method as claimed in claim 44 wherein the compound applied is 1-t-butyl-2-(1,2,4-triazol-1-yl)-2-p-fluorobenzyl-ethanol.

51. A method as claimed in claim 44 wherein the compound applied is 1-t-butyl-2-(1,2,4-triazol-1-yl)-2-p-bromobenzyl-ethanol.

52. A method as claimed in claim 44 wherein the compound applied is 1-t-butyl-2-(1,2,4-triazol-1-yl)-2-(2'-chloro-4'-fluorobenzyl)ethanol.

53. A method as claimed in claim 44 wherein the compound applied is 1-t-butyl-2-(1,2,4-triazol-1-yl)-2-o-methylbenzyl-ethanol.

54. A method as claimed in claim 44 wherein the compound applied is 1-t-butyl-2-(1,2,4-triazol-1-yl)-2-p-methylbenzyl-ethanol.

55. A method as claimed in claim 44 wherein the compound applied is 1-t-butyl-2-(1,2,4-triazol-1-yl)-2-(2',4'dichloro-benzyl)ethanol.

* * * * *